United States Patent
Bibian et al.

(10) Patent No.: US 10,463,272 B1
(45) Date of Patent: *Nov. 5, 2019

(54) PHYSIOLOGICAL ELECTRODE ASSEMBLY FOR FAST APPLICATION

(71) Applicants: Stéphane Bibian, Cleveland Heights, OH (US); Tatjana Zikov, Cleveland Heights, OH (US)

(72) Inventors: Stéphane Bibian, Cleveland Heights, OH (US); Tatjana Zikov, Cleveland Heights, OH (US)

(73) Assignee: NeuroWave Systems Inc., Cleveland Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,776

(22) Filed: Jan. 11, 2018

Related U.S. Application Data

(63) Continuation of application No. 14/701,944, filed on May 1, 2015, now Pat. No. 9,901,278, which is a continuation of application No. 14/324,719, filed on Jul. 7, 2014, now Pat. No. 9,050,015, which is a continuation of application No. 14/058,709, filed on Oct. 21, 2013, now Pat. No. 8,805,469, which is a continuation of application No. 13/110,505, filed on May 18, 2011, now Pat. No. 8,594,763.

(60) Provisional application No. 61/348,151, filed on May 25, 2010.

(51) Int. Cl.
*A61B 5/0478* (2006.01)
*A61B 5/0492* (2006.01)
*A61B 5/0496* (2006.01)
*A61B 5/042* (2006.01)
*A61B 5/00* (2006.01)
*A61B 5/0408* (2006.01)

(52) U.S. Cl.
CPC ............ *A61B 5/0478* (2013.01); *A61B 5/042* (2013.01); *A61B 5/0492* (2013.01); *A61B 5/0496* (2013.01); *A61B 5/6833* (2013.01); *A61B 5/0408* (2013.01); *A61B 5/6839* (2013.01); *A61B 2562/0209* (2013.01); *A61B 2562/14* (2013.01); *A61B 2562/242* (2013.01)

(58) Field of Classification Search
CPC .................................................... A61B 5/0478
See application file for complete search history.

(56) References Cited

U.S. PATENT DOCUMENTS

| | | | | |
|---|---|---|---|---|
| 8,594,763 | B1 * | 11/2013 | Bibian | A61B 5/0478 600/372 |
| 8,805,469 | B1 * | 8/2014 | Bibian | A61B 5/0478 600/383 |
| 9,050,015 | B2 * | 6/2015 | Bibian | A61B 5/0478 |

* cited by examiner

*Primary Examiner* — Lee S Cohen
(74) *Attorney, Agent, or Firm* — Brian Kolkowski

(57) ABSTRACT

The present invention relates to a physiological recording electrode, and, more particularly, to an EEG (electroencephalography) recording electrode that can be used without the need for numerous steps in preparing the subject's skin and the electrode itself. The invention further relates to a surface feature or penetrator with a size and shape which that will not bend or break, which limits the depth of application, and/or anchors the electrode or other device during normal application; and a packaging system comprising a well and electrolytic fluid for maintaining a coating of said electrolytic fluid on the surface feature or penetrator.

6 Claims, 12 Drawing Sheets

PHYSIOLOGICAL ELECTRODE ASSEMBLY FOR FAST APPLICATION

CROSS-REFERENCE TO RELATED APPLICATIONS

This application claims priority to U.S. patent application Ser. No. 14/701,944, filed on May 1, 2015, which issued into U.S. Pat. No. 9,901,278, which claimed priority to U.S. patent application Ser. No. 14/324,719, filed on Jul. 7, 2014, which issued into U.S. Pat. No. 9,050,015, which claimed priority to U.S. patent application Ser. No. 14/058,709, filed on Oct. 21, 2013, which issued into U.S. Pat. No. 8,805,469, which claimed priority to U.S. patent application Ser. No. 13/110,505, filed on May 18, 2011, which issued into U.S. Pat. No. 8,594,763, and which claimed priority to U.S. Provisional Patent Appln. Ser. No. 61/348,151, which was filed on May 25, 2010.

BACKGROUND OF THE INVENTION

1. Field of the Invention

The present invention relates to a physiological recording electrode, and, more particularly, to an EEG (electroencephalography) recording electrode that can be used without the need for numerous steps in preparing the subject's skin and the electrode itself. The invention further relates to a surface feature or penetrator with a size and shape which that will not bend or break, which limits the depth of application, and/or anchors the electrode or other device during normal application; and a packaging system comprising a well and electrolytic fluid for maintaining a coating of said electrolytic fluid on the surface feature or penetrator.

2. Technology Review

Electrodes for measuring biopotential are used extensively in modern clinical and biomedical applications. These applications encompass numerous physiological tests including electrocardiography (ECG), electroencephalography (EEG), electrical impedance tomography (EIT), electromyography (EMG) and electro-oculography (EOG). The electrodes for these types of physiological tests function as a transducer by transforming the electric potentials or biopotentials within the body into an electric voltage that can be measured by conventional measurement and recording devices.

In general, most commercial EEG electrodes for these applications today are placed on the surface of the skin, which is a layered structure consisting of the epidermis and the dermis. The dermis contains the vascular and nervous components. Further it is the part of the skin where pain has its origins. The epidermis, however, contains no vascular or nervous components and is made up of several layers, including the Stratum basale or stratum germinativum, stratum spinosum, stratum granulosum, stratum lucidum, and the stratum corneum.

The stratum corneum, the outermost layer of the skin, is the primary source of high electrical impedance and, thus, this layer dramatically influences the biopotential measurements. The stratum corneum is very thin and uniform in most regions of the body surface ranging from 13-15 µm with a maximum of about 20 µm. If the high impedance results from the stratum corneum can be reduced, a more stable electrode will result. Therefore with existing physiological electrodes the skin must be prepared prior to application when lower impedance is required.

The most common electrode preparation methods to avoid the high impedance effects of the stratum corneum are: 1) shaving the hair from the skin; and either 2a) abrading the stratum corneum or 2b) using an electrolytic gel. Electrodes requiring the use of an electrolytic gel or fluid are often referred to as "wet" electrodes. Hair is shaved from the skin to improve the contact between the electrodes and the skin surface. The goal of the abrasion of the stratum corneum is to reduce the thickness of (or remove) the stratum corneum (and therefore its electrically insulating characteristics).

Drawbacks of abrading the skin are that the abraded area regenerates dead cells fairly quickly (resulting in a limited time period for using the electrode), and if the abrasion is too deep the person can experience pain. Additionally, electrolytic gels or fluids may be applied to abraded surface to enhance the contact. Alternatively, electrolytic gels or fluids can be applied to the surface of the skin directly. The electrolytic gel having a high concentration of conductive ions diffuses into the stratum corneum and improves its conductivity. Drawbacks observed with the use of electrolytic gels or fluids involve the change of conductivity with time as the gels dry, discomfort (an itching sensation) at the patient's skin as a result of the gels drying, and the possibility of a rash due to an allergic reaction to the electrolytic gels.

Further drawbacks of "wet" electrodes include skin preparation and stabilization of the electrode with respect to the skin surface. This is because movement of the electrode on the surface of the skin causes the thickness of the electrolytic layer (formed by the electrolytic gels or fluids) to change resulting in false variation in the measured biopotential. Some electrode designs have an adhesive backing to reduce the movement of the electrode on the skin surface; however, this feature does not eliminate completely the movement of the electrode with respect to the subject's skin. Another drawback is the length of time required to prepare the skin and apply the electrolytic gels or fluids prior to measurement of the biopotentials.

More recently, dry electrodes have been developed which eliminate many of these limitations by foregoing the need for electrolytic fluids, gels, or colloids. For example, in Schmidt (U.S. Pat. No. 6,782,283) a dry electrode containing a surface feature or penetrator is used to penetrate the stratum corneum of the skin and conduct a signal without the aid of electrolytic fluid. The design of Schmidt is such that the electrode's surface feature or penetrator(s) pierce, break, or create entry through the high impedance layers of the subject's skin, and thus come in contact with the more electrically conductive layers which facilitates the transmission of biopotential signals.

The downside to Schmidt is that it teaches against the use of electrolytic fluid, gel or colloid at all. However, use of a dry electrode with such electrolytic fluid, gel, or colloid unexpectedly enhances the conductivity of biopotential signals being collected from a subject, particularly with weaker biopotential signals such as EEG signals.

In view of the foregoing inherent disadvantages with presently available wet and dry electrodes, it has become desirable to develop an electrode that does not require skin preparation or the use of electrolytic gels and overcomes the inherent disadvantages of presently available dry electrodes.

SUMMARY OF THE INVENTION

The present invention relates to a physiological recording electrode or electrode array, and, more particularly, to a physiological recording electrode or electrode array that can be used without the need for numerous steps in preparing the subject's skin and the electrode itself. The electrode or electrode array preferably requires little or no preparation of the subject's skin. The invention further relates to an electrode or an array of electrodes where the surface of the electrodes comprises shapes or surface feature or penetrators that either penetrate through the stratum corneum layer of the epidermis or create access to the lower levels of the epidermis by cracking or breaking small areas of the stratum corneum to create entry or a via to lower layers of the epidermis. These features or penetrators preferably have a size and shape which prevents bending or breaking, which limits the depth of application, and/or anchors the electrode or other device during normal application; and a packaging system comprising a well and electrolytic fluid providing a surface coating of electrolytic fluid on the surface features or penetrator.

The present invention, in its various embodiments, is intended to address many of the shortcomings of physiological electrodes currently available. Surface electrodes are an extremely important tool for the monitoring and recording of physiological signals. Therefore, it is important that these electrodes be capable of providing the clearest, cleanest signal possible and also to be easy to use to decrease the time it takes to begin monitoring a subject's signal(s).

The present invention utilizes an electrolytic fluid, gel, or colloid to coat the surface of the surface features or penetrators. Unlike previous physiological recording devices requiring the use of such fluid, gels or colloids, the present invention does not require the fluid, gel, or colloid to be applied to the subject or patient separately and before the electrode is put into place. Thus, the present invention seeks to eliminate, or at least minimize, the length and degree of skin preparation required to apply the electrode as well as the mess that accompanies the use if separate fluids, gels, or colloids. This electrolytic fluid preferably is such that will enhance the conductivity of biopotential signals from the subject to the recording or measuring device by reducing electrical impedance. Generally, electrolytic fluids, gels and colloids are designed with a high concentration of conductive ions, and as the fluid, gel or colloid diffuses into the subject's stratum corneum it aids in conducting the biopotential signal through that layer. The present invention does not rely solely on the electrolytic fluid, gel, or colloid to conduct the signal across the stratum corneum, but rather utilizes the increased conductivity to transfer the signal to the surface features or penetrators which also pierce, break, or create entry through the stratum corneum. This has the added benefit of minimizing the problems that arise through increased thickness of the conductive layer due to the thickness of the fluid, gel or colloid layer as well as the potential drastic loss of conductivity when the fluid, gel, or colloid dries over time.

The present invention further utilizes a packaging base layer which forms a base to which the electrode or electrode array can be attached for storage. This packaging base layer preferably comprises an upper surface which the electrode or electrode array can attach to, and a well to hold electrolytic fluid and into which the surface feature or penetrator(s) can extend. This layer can be made of almost any type of material that does not react with the gels or electrolytic materials being placed in the well. Preferably this layer is a plastic. More preferably different types of plastics can be used, including but not limited to polyvinyl chloride, polystyrene, polyamide, polyethylene, polypropylene, polyurethane, Teflon, and the like; though it is not limited only to plastics, and is designed to be used with other materials as well (i.e., metal, paper, rubber, and the like). Preferably, the materials used for the packaging base layer may be coated with a substance in order to allow for the various adhesive portions of the device to be removable without losing their adhesive quality.

The adhesive may be of any variety known to those having skill in the art which are capable of securing the various portions of the present invention together for transportation and storage purposes, but that allow the electrode or array to be removed from the package and then placed securely on the subject or patient without losing its adhesive capabilities. The adhesive must be capable of being removed and reapplied to another surface without slipping, sliding, peeling off, or otherwise moving while in use.

An important aspect of many embodiments of the present invention is the surface features or penetrators designed to pierce, break, or create entry through the tough, non-conductive outer layers of the skin. Many types of surface features are available for this purpose including but not limited to ridges, columns, penetrators, anchors, epidermal stops, and combinations thereof. Preferably, there is at least one surface feature protruding from the electrode's lower surface. One of the important functions of the configuration of surface features is to displace or move the hair, dead skin cells and/or detritus so that the surface features can better collect the electrical biopotentials generated by the body.

The ridge(s) as used in the present invention is preferably a long, narrow structure or elevation. The ridge(s) can have a variety of cross sections over a length. Examples of these cross sections include but are not limited to a square, rectangle or trapezoid, a pointed surface like that of a triangle, a domed surface like that of an arch or arc, a cross section with a concave surface between to ridge lines forming the two ridge lines, some other unique cross-section or the like. The cross section of the ridge extends for a length. The length of the ridge is preferably substantially longer than the height or width of the cross-section of the ridge. The surface of the ridge away from the substrate, when applied to the skin surface, depresses, but does not need to pierce the skin but anchors the electrode in place to prevent motion artifacts, to displace hair, dead skin cells and/or detritus, to increase the surface area of the electrode in contact with the skin, and to be capable, in part, of transmitting an electric potential which can be measured from the surface of the skin through the ridge.

A column(s) is another type of structure or elevation that can be used in the present invention. A column(s) can have a variety of cross sections over a length. Examples of these cross sections include but are not limited to a square, rectangle or trapezoid, a pointed surface like that of a triangle, a domed surface like that of an arch or arc, a cross section with a concave surface between two points (wherein the distance from the base to either point is greatest height of the column for the cross-section), some other unique cross-section or the like. The cross section of the column like a ridge extends for a length. However, the width of the column is preferably in proportion to the height of the cross-section of the column, and more preferably shorter than the height of the column. The surface of the column away from the substrate, when applied to the skin surface, depresses, and does not easily pierce the skin but anchors the electrode in place to prevent motion artifacts, to displace hair, dead skin cells and/or detritus, to increase the surface area of the electrode in contact with the skin, and to be capable, in part, of transmitting an electric potential which can be measured from the skin through the ridge.

A penetrator(s) is also a surface feature that can be used in the present invention. The penetrator(s) is sized and shaped for piercing the stratum corneum or outer layer of the epidermis, and accessing the lower layers of the epidermis. The penetrator can take many shapes including but not limited to pyramidal, needle-like, triangular, or any other shape that can be tapered to a point or tip. The surface of the penetrator away from the substrate, when applied to the skin surface, readily pierces the skin, preferably anchors the electrode in place to prevent motion artifacts or any substantial movement, increases the surface area of the electrode in contact with the skin and lower layers of the epidermis, and is capable, in part, of transmitting an electric potential which can be measured from the skin and lower layers of the epidermis through the penetrator.

The epidermal stop(s), which can be used in the present invention, is a structure or elevation. Epidermal stops are structures of a particular height with respect to the height of the penetrator(s) or other surface features so as to prevent the penetrator(s) or other surface features such as columns and ridges from penetrating into the dermis of the skin or unduly distorting the surface of the skin, respectively, where they might cause discomfort to the subject. An epidermal stop(s) may also be incorporated into a penetrator, ridge, column or like surface feature or can be a separate surface feature. The epidermal stops may, however, have any shape known to those skilled in the art that would effectively prevent the penetrator(s) from entering the dermis of the skin, or from being applied to deeply. The epidermal stops are preferably applied in an array among the penetrators, therefore further minimizing inadvertent deep penetration or over penetration by the penetrator(s) or minimizing significant distortion of the skin by other surface structures. If the epidermal stop is a separate surface feature or incorporated into another structure, preferably, the epidermal stop in combination with at least one other surface feature or two structures with incorporated epidermal stops create a detritus trough.

A detritus trough is the area interposed between adjacent surface structures or features. These troughs, when provided or naturally occurring in the design, allow for a more accurate placement of the surface features by allowing for displacement of the hair and other detritus on the skin in these troughs. Preferably, the detritus troughs are sufficient in number and size to allow for placement of the device on skin with a significant amount of hair such as for example the scalp or the chest of a male subject. Detritus troughs are created to maximize the area available for optimal device to skin contact, by improving the probability that hair and other detritus will enter the troughs and not preventing the surface features from either coming in contact with the skin or penetrating the skin. Thus detritus troughs may be parallel to one another, perpendicular to one another, or in any other orientation made to improve the contact of the device with the skin of the subject.

An anchor(s), which can be used in the present invention is a structure or elevation that stabilizes the physiological device against a subject's skin. This stabilization further preferably prevents motion artifacts in the electrophysiological signal from the device, or any substantial movement. While the anchor can also be any of the structures described above, the anchor may also serve no other purpose except to stabilize or reduce movement of the device on the subject's skin. The anchor(s) can have a variety of cross sections over a length as described above for the various surface structures.

The present invention is designed to be used in connection with the collection, conducting, measuring, and/or monitoring of biopotential signals. These biopotential signals may include electrocardiography (ECG), electrical impedance tomography (EIT), electromyography (EMG), electro-oculography (EOG), and most preferably electroencephalography (EEG).

One embodiment of the present invention involves a physiological recording device comprising a packaging base layer comprising a well containing a sponge and electrolytic fluid, and at least one physiological recording electrode comprising an adhesive collar and a physiological electrode comprising an upper and a lower surface, and at least one surface feature protruding from the lower surface of the physiological electrode, wherein the sponge holds the electrolytic fluid in contact with the at least one surface feature until the physiological recording electrode is removed for placement on a subject.

Another embodiment of the present invention involves a physiological recording device comprising a packaging base layer comprising a well containing a colloid with electrolytic fluid, and at least one physiological recording electrode comprising an adhesive collar and a physiological electrode comprising an upper and a lower surface, and at least one surface feature protruding from the lower surface of the physiological electrode, wherein the colloid holds the electrolytic fluid in contact with the at least one surface feature until the physiological recording electrode is removed for placement on a subject.

Yet another embodiment of the present invention involves a physiological recording device comprising a packaging base layer comprising a well containing a sponge with electrolytic fluid, and at least one physiological recording electrode comprising an adhesive collar and a physiological electrode comprising an upper and a lower surface, and at least two surface features protruding from the lower surface of the physiological electrode, wherein the sponge holds the electrolytic fluid in contact with the at least two surface features until the physiological recording electrode is removed for placement on a subject.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in, and constitute a part of, this specification. The drawings illustrate various embodiments of the invention and together with the description serve to explain the principles and operation of the many embodiments of this invention.

DETAILED DESCRIPTION OF THE DRAWINGS

Figure 1:
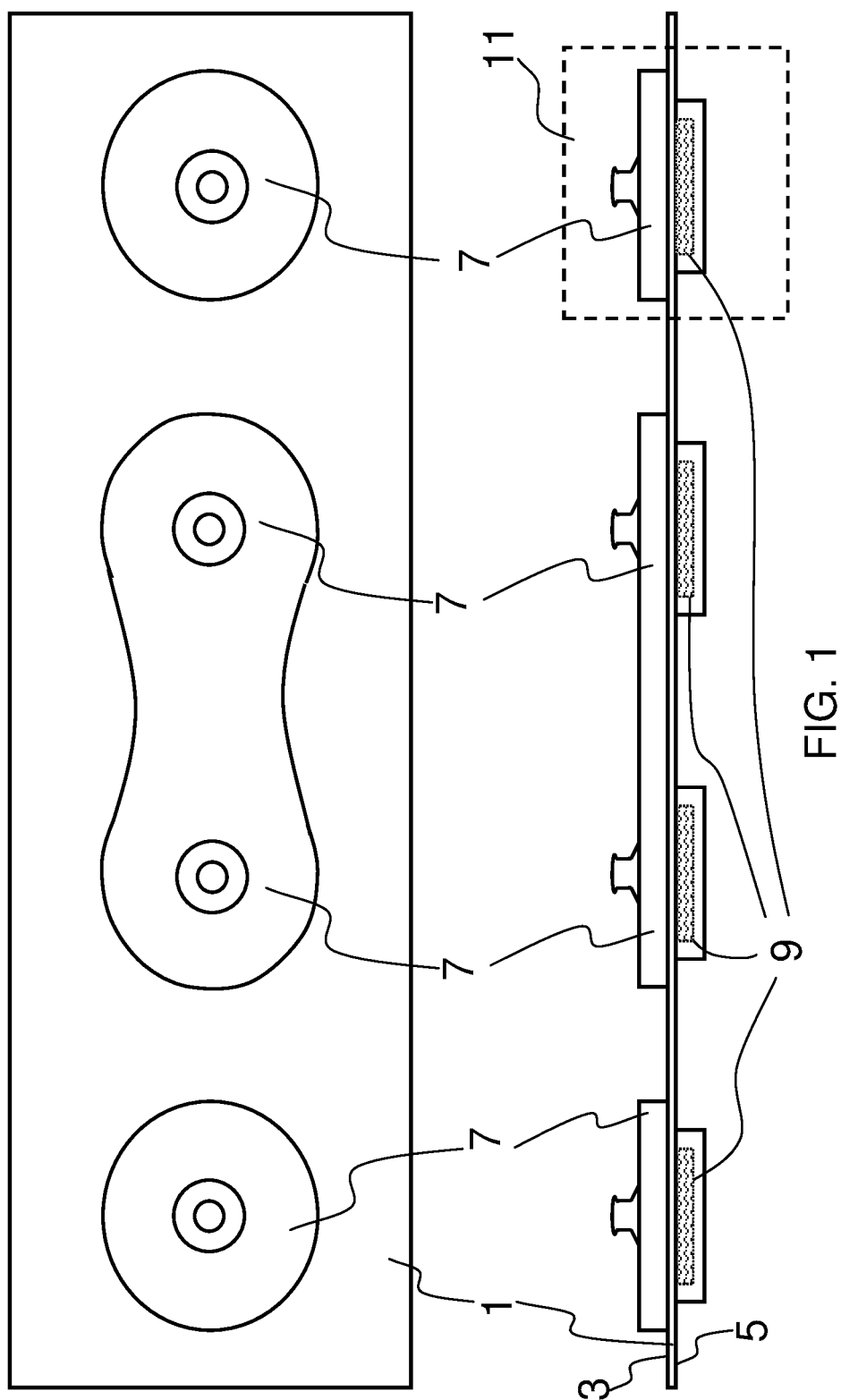
FIG. 1. Aerial and side views of one embodiment of electrodes packaged in an electrolytic gel well where the well is attached to the bottom of a separator.

Various embodiments of the methods of the present invention include one or more of the following components, and variations thereof. One of these components includes a packaging base layer comprising a well containing a sponge and electrolytic fluid. The packaging base layer itself provides a foundation for the electrode to be attached to or rested upon. The packaging base layer is preferably made of a material, and of dimensions, that allow it to be flexible. This packaging base layer can be made of any material that will allow the adhesive collar of the electrode to adhere to its surface while still allowing it to peel away. Further, the wells may be created by any number of methods including, but not limited to, drilling them into the packaging base layer, grinding them out of the packaging base layer, creating the entire packaging base through various methods of molding, and the like. Preferably, the packaging base is made of a cheap material, such as plastics, to keep manufacturing costs low. Specific plastic fabricating techniques that could be used to create the packaging base include, but are not limited to, extrusion, injection molding, compression molding, reaction injection molding, vacuum forming, and the like.

One embodiment of the present invention involves a packaging base layer that is made of a thin packaging base layer with a gel well attached to the lower surface. This packaging base layer is preferably made of a material, and of dimensions that allow it to be flexible. This packaging base layer can be made of any material that will allow the adhesive collar of the electrode to adhere to its surface while still allowing it to peel away (i.e. plastics as described above, metal, and the like). This layer can be made of almost any type of plastic, including but not limited to polyvinyl chloride, polystyrene, polyamide, polyethylene, polypropylene, polyurethane, Teflon, and the like, or other materials such as metals. Preferably, the packaging base layer is constructed of such a material as to be disposable. In other words, once the product is opened, and the physiological recording electrodes removed to be placed on a subject or patient, the user should preferably be able to discard the packaging base layer in the trash, and not need to follow any special or particular disposal instructions (i.e., biohazard procedures). The well can similarly be made of any such material. For this packaging method, an aperture or hole must be cut in the packaging base layer and the gel well attached to the lower surface aligned with the hole in the packaging base layer. This creates the well where medium containing the electrolytic fluid can be placed.

The medium containing the electrolytic fluid can be any porous material, such as to a sponge, or colloidal suspension placed inside the well for purposes of holding electrolytic fluid and keeping said fluid in contact with the surface feature or penetrators of the electrode when the electrode is affixed to the upper surface of the packaging base layer. When the electrode is affixed as such, the surface feature or penetrators extend through the aperture and into the sponge or colloid where they are submersed in the electrolytic fluid and become coated with same. The electrolytic fluid is generally of sufficient viscosity that when the electrode is removed from the packaging layer, a coating of the electrolytic fluid remains on the surface of the surface feature or penetrators, thereby enhancing their conductive properties for the purpose of transmitting biopotential signals from the subject's body to the monitoring equipment.

Another component of various embodiments of the present invention includes at least one physiological recording electrode comprising an adhesive collar, an upper and lower surface, and a connection node. The adhesive collar is preferably constructed of material that is capable of transferring moisture to avoid sweating when attached to the subject's skin, thus preventing slipping of the electrode. The connection node is a piece that may be molded into a single piece with the rest of the electrode body or a separate piece assembled onto the electrode body. The node is preferably molded or attached to the upper surface of the electrode such that when the electrode is attached to a subject or patient, the connection node extends up away from the subject. The node creates a connection point for the electrode leads which are connected to the appropriate monitoring equipment.

Preferably, the physiological recording electrode comprises at least one surface feature or surface feature or penetrator protruding from the lower surface of the physiological electrode that is capable of piercing, breaking, or creating entry through the stratum corneum layer or outer layer of a subject's skin. The surface feature(s) or surface feature or penetrator(s) may or may not be coated with a conductive material, such as silver, gold, or other material such as silver-silver chloride. This coating preferably is one that maintains or is likely to maintain an electrical attraction to electrolytic fluids that may be used to further coat the surface of the surface feature or penetrator to facilitate the transmission of physiological signals.

Now referring to the FIGS. 1-10, FIG. 1 is both an aerial and side view of one embodiment of the present invention wherein at least one physiological electrode 7 is packaged in such a manner that the at least one surface feature or penetrator 21 extends into a well 9 containing or holding electrolytic fluid 23. The electrolytic fluid 23 may be infused into a porous material 27 such as a sponge 27, it may be dispersed into a colloidal suspension 27 with some dispersion medium (not shown), it may be a viscous fluid with properties described herein contained by the well, or other method currently known or developed in the future. The packaging base layer 1 provides a substrate comprising an upper surface 3 and a lower surface 5. Physiological recording electrodes or arrays comprising electrodes 7 (comprising at least a physiological recording electrode and an adhesive collar 15) are attached to the upper 3 surface via the attached adhesive collar 15. Although the figure depicts four such electrodes 7, the two center electrodes comprise a two electrode array, whereas the two outside electrodes 7 are individual electrodes. The upper surface 3 preferably comprises a smooth surface which allows for temporary adhesion of the electrode's 7 adhesive collar 15, but also allows the electrodes or electrode array to be removed without loss of the adhesive quality for secure attachment of the electrodes and electrode array to a subject or patient. The electrode(s) 7 are placed on the packaging layer 1 in such a manner that the electrode 7 is aligned with an aperture (not shown) through the packaging layer and at least one surface feature or penetrator 21 on the electrode extends into the packaging well 9. The well 9 preferably contains a sponge or other porous material 27 infused with electrolytic fluid 23, or a colloidal suspension 27 containing electrolytic fluid 23. The surface feature or penetrators 21 thereby remain bathed in the electrolytic fluid 23 throughout their time in the packaging regardless of how they are stored, and are thus coated with said fluid when removed from the packaging layer 1 and are ready for application onto a subject. Callout 17 is depicted in greater detail in FIGS. 2-5, and depicts various features of the present invention.

Figure 2:
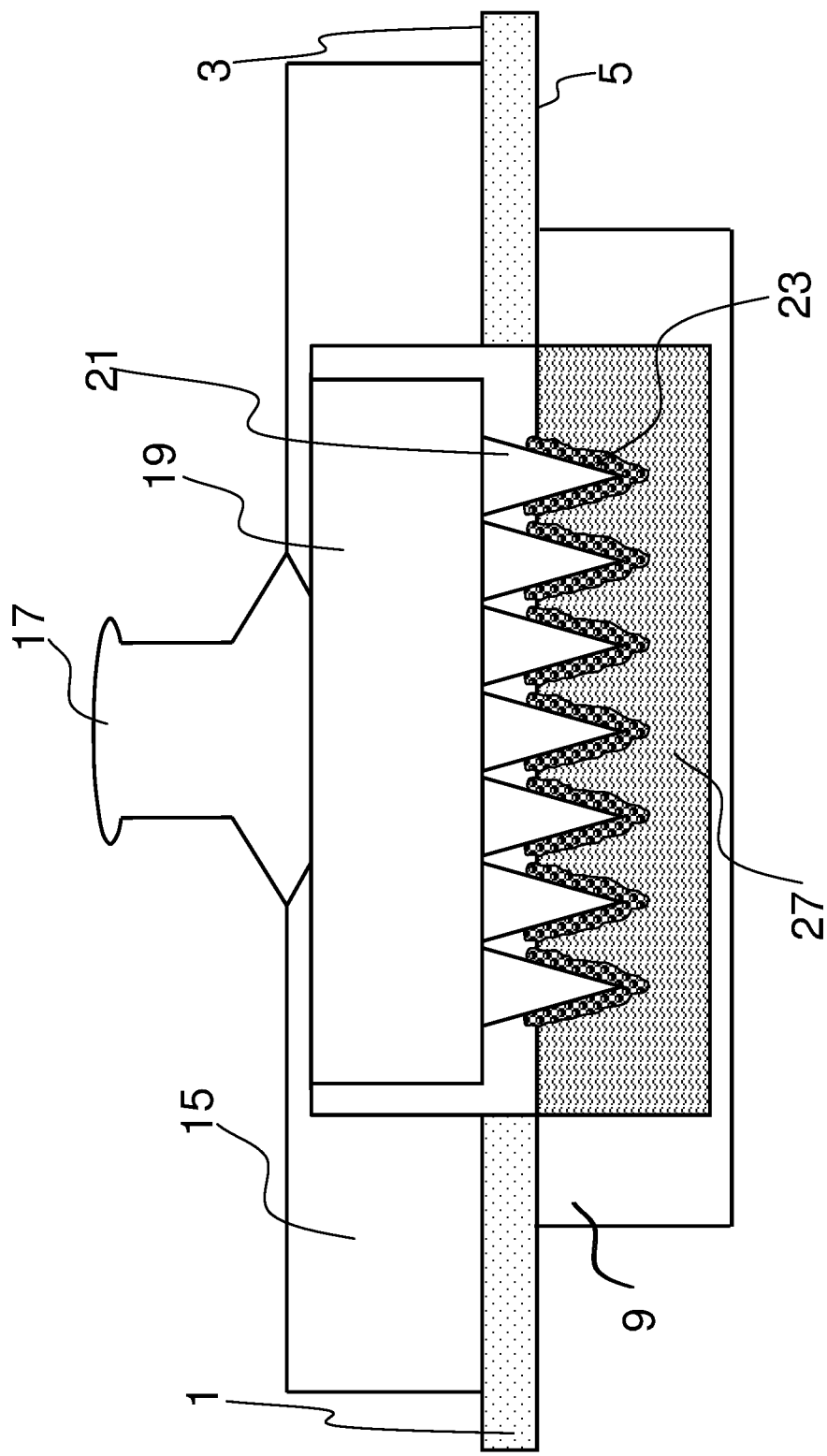
FIG. 2. Cross-sectional view of an electrode with the surface feature or penetrators resting in a gel well attached to a separator.

FIG. 2 is a cross-sectional view of one embodiment of the present invention and callout 17 from FIG. 1 wherein an electrode 7 is attached to a packaging system comprising a base layer 1 with an electrolytic fluid 9 well attached to, or formed in, the bottom of the base layer.

In this particular embodiment, the packaging base layer 1 comprises a thin layer of material such as plastic. This layer can be made of almost any type of material that does not react with the gels or electrolytic materials being placed in the well. Preferably this layer is a plastic. More preferably different types of plastics can be used, including but not limited to polyvinyl chloride, polystyrene, polyamide, polyethylene, polypropylene, polyurethane, Teflon, and the like; though it is not limited only to plastics, and is designed to be used with other materials as well (i.e., metal, paper, rubber, and the like). The upper surface 3 of the packaging base layer 1, acts as an attachment surface for the electrode 7. This upper surface 3 preferably is smooth and non-binding such that allows the electrode assembly to be removed from the surface without sticking and without loss of the adhesive substance used to attach the electrode to a subject or patient. The lower surface 5 of the packaging base layer can act as an attachment surface for the electrolytic fluid well 9. The lower surface 5 of the packaging base layer 1 preferably is able to maintain a strong bond between itself and the well's adhesive edges to avoid separation and prevent leakage or loss of electrolytic fluid. The packaging base layer 1 further preferably comprises apertures or holes (not labeled) through the entire layer 1 such that the electrode 7 attached to the upper surface 3 and the electrolytic fluid well 9 attached to the lower surface 5 are in alignment, and the electrode, with at least one surface feature or penetrator 21, may extend through said aperture or hole to be held in contact with the electrolytic fluid 23 or colloid 27 contained in the well 9.

The electrode assembly preferably comprises at least an adhesive collar 15, an electrode body 19, a connection node 17 which is formed with or attached to the electrode body, and at least one surface feature or penetrator 21, capable of piercing or breaking the stratum corneum 35 of a subject's skin. The adhesive collar 15 preferably comprises a material such as a foam material or a breathable polymer which provides flexibility as well as support, and an adhesive layer (not shown) which may consist of a very thin coating of said adhesive on the bottom surface of the lower or outer portion of the collar 15 and which is used to attach the electrode assembly first to the package 1, and then subsequently to a subject's skin or body. Also preferably, the electrode assembly contains at least one surface feature or penetrator 21 as part of the electrode body 19 which is capable of piercing or creating an opening in a stratum corneum 35 layer or outer layer of a subject's skin. This electrode is then placed in contact with the upper surface 3 of the packaging base layer 1 in such a manner that the electrode body 19 and the at least one surface feature or penetrator 21 are in line with an aperture or hole (not labeled) through the base layer and the at least one surface feature or penetrator 21 extends through the aperture or hole and is held in place by virtue of the adhesive on the adhesive collar 15.

The electrolytic fluid well preferably comprises at least a pocket or well 9 attached to the lower surface 5 of the packaging layer 1 with an adhesive (not shown), and a medium 27 for holding electrolytic fluid which may comprise a sponge, a colloidal suspension, or some other device capable of holding the fluid in contact with the surface feature or penetrator 21. In the present embodiment, the electrolytic fluid well 9 may be created by means of an adhesive collar that is either similar or identical to the adhesive collar 15 used to attach the electrode assembly to the packaging layer 1 and the subject or patient. If the electrolytic fluid 23 is infused into a sponge 27, the sponge may be any porous material placed inside the well 9 for purposes of absorbing and holding electrolytic fluid. If the electrolytic fluid 23 is dispersed into a colloidal suspension or disc 27, the continuous phase, or dispersion medium can be of any type that will readily hold the particular electrolytic fluid being used while allowing the at least one surface feature or penetrator 21 of the electrode to be held in contact with the medium 27 and coated by the electrolytic fluid 23. The adhesive used to attach the fluid well to the lower surface of the packaging layer 5 preferably is a permanent adhesive and is different from that used to attach the electrode 7 to the upper surface 3. Similar to the electrode 7, the electrolytic fluid well 9 is attached to the lower surface 5 in such a manner that the well is aligned with the aperture or hole (not labeled) in the packaging base layer 1. As such, the at least one surface feature or penetrator 21 of the electrode 7 extends through the aperture and into the electrolytic well 9, more specifically into the electrolytic fluid medium 27, where it comes into contact with the electrolytic fluid 23 maintaining a coating of said fluid on the surface feature or penetrator 21.

Alternatively, the electrolytic fluid well 9 may comprise a multiple piece system (not shown) in which an open adhesive collar (not shown) is used and which requires the placement of a base layer over the opening not in contact with the packaging base layer to prevent loss or leakage of electrolytic fluid. Similarly, a multiple piece system as described could be used with the electrode assembly as well, where the base layer is attached to the opening of the electrode adhesive collar 15 and is further used to connect that collar to the electrode body 19.

The surface feature(s) or penetrator(s) 21 of the electrode body remain in constant or regular contact with electrolytic fluid 23 throughout the time the electrode 7 remains attached to the package 1. The present invention is designed so that when the electrode 7 is removed from the package 1, the at least one surface feature or penetrator 21 maintains a coating of the electrolytic fluid 23 and no external application of electrolytic fluid is necessary. This eliminates an extra and uncertain step from the application process.

In many cases, the at least one surface feature or penetrator 21 is coated in some conductive substance, such as a silver/silver chloride, which facilitates the conduction of electrical biopotential signals from the subject or patient to the monitoring equipment. Preferably, the electrolytic fluid used is designed to maintain a surface attraction to the conductive coating on the penetrator(s) to aid in the electrolytic fluid remaining 23 attached or attracted to the surface of the surface feature(s) or penetrator(s) 21.

Figure 3:
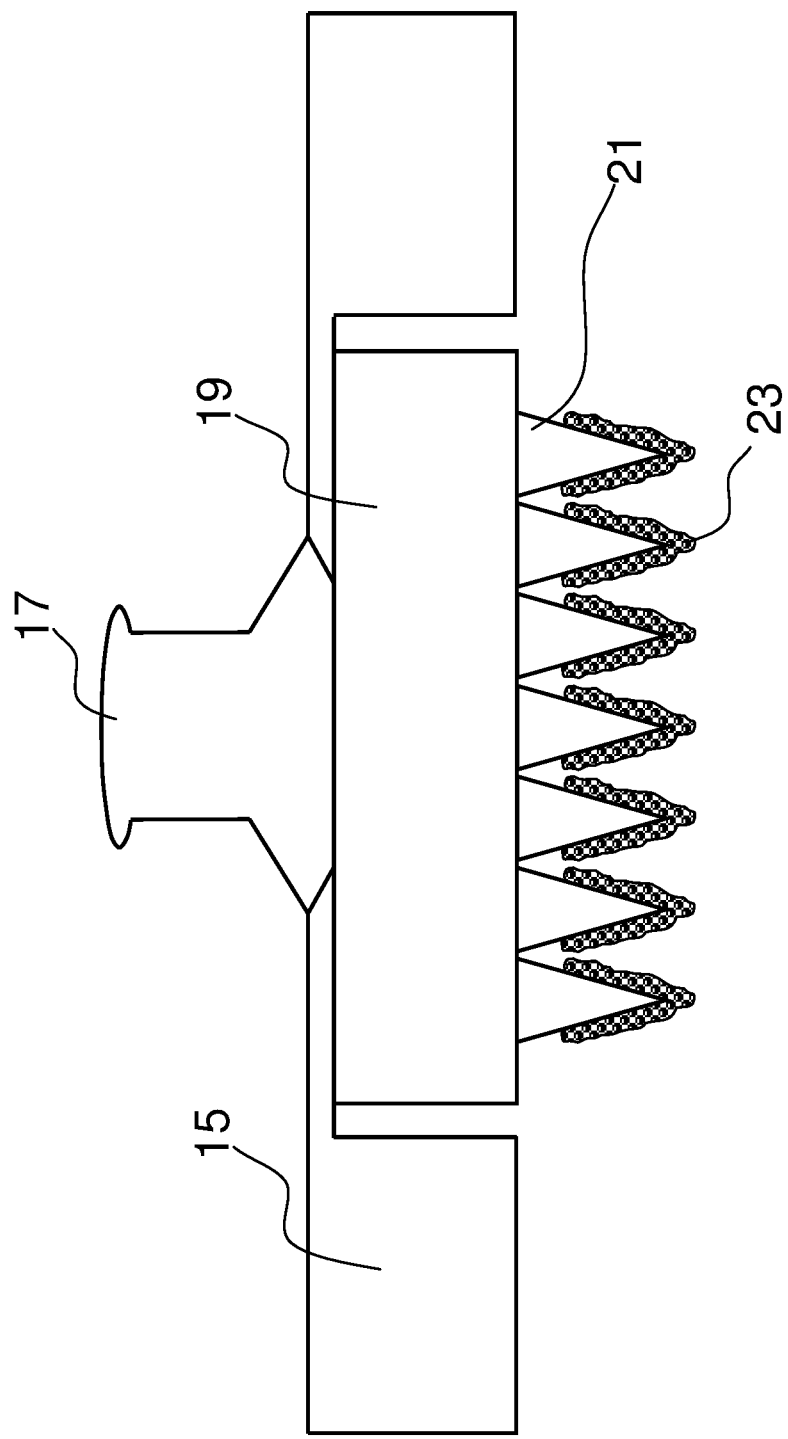
FIG. 3. Cross-sectional view of an electrode removed from the packaging with electrolytic fluid coating the surface feature or penetrator(s).

FIG. 3 is a cross-sectional view of one embodiment of the present invention wherein an electrode is removed from the packaging system.

The electrode assembly preferably comprises at least an adhesive collar 15, an electrode body 19, a connection node 17 which is attached to the electrode body 19, and at least one surface feature or penetrator 21, capable of piercing the stratum corneum 35 of a subject's skin. The adhesive collar 15 preferably comprises a material such as a foam rubber or sponge-like material which provides flexibility as well as support, and an adhesive layer (not shown) which may consist of a very thin coating of said adhesive on the lower or outer portion of the collar 15 and which is used to attach the electrode assembly first to the upper surface 3 of the package 1, and then subsequently to a subject's skin or body (not shown). Also preferably, the electrode assembly contains at least one surface feature or penetrator 21 as part of the electrode body 19 which is capable of piercing or creating an opening in a stratum corneum 35 layer or outer layer of a subject's skin. This electrode assembly is then placed in contact with the upper surface 3 of the packaging base layer 1 in such a manner that the electrode body 19 and the at least one surface feature or penetrator 21 are in line with an aperture or hole (not labeled) through the base layer 1 and the at least one surface feature or penetrator 21 extends through the aperture or hole and is held in place by virtue of the adhesive on the adhesive collar 15.

The surface feature or penetrator(s) 21 of the electrode body 19 remain in constant contact with electrolytic fluid 23 throughout the time the electrode assembly remains attached to the package 1. The present invention is designed so that when the electrode assembly is removed from the package, the at least one surface feature or penetrator 21 maintains a coating of the electrolytic fluid 23 and no external application of electrolytic fluid is necessary. This eliminates an extra step from the application process.

Additionally, the present invention may be used with dry electrodes which do not require the application of electrolytic fluid. In these cases, the present invention allows the surface feature or penetrator(s) to maintain a slight, thin coating of fluid 23 which further aids the conduction of signals.

In many cases, the at least one surface feature or penetrator 21 is coated in some conductive substance (not shown), such as a silver/silver chloride, which facilitates the conduction of electrical biopotential signals from the subject or patient to the monitoring equipment. Preferably, the electrolytic fluid 23 used is designed to maintain a surface attraction to the conductive coating (not shown) on the surface feature or penetrator(s) 21 to aid in the electrolytic fluid 23 remaining attached or attracted to the surface of the surface feature or penetrator(s) 21.

Figure 4:
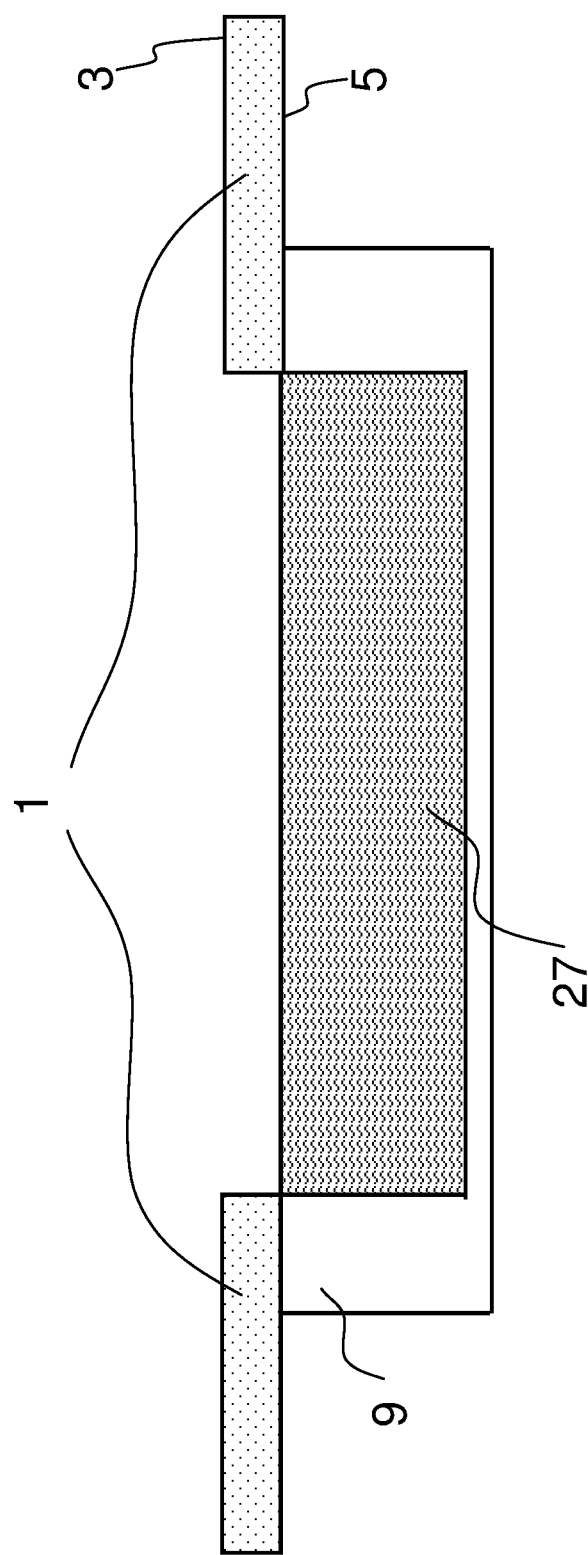
FIG. 4. Cross-sectional view of gel well with separator.

FIG. 4 is a cross-sectional view of one embodiment of the present invention wherein an electrolytic fluid well is attached to a packaging system comprising a base layer and an aperture or hole.

The electrolytic fluid well preferably comprises at least a pocket or well 9 attached to the lower surface 5 of the packaging layer 1 with an adhesive (not shown), and a medium for holding electrolytic fluid 27 which may comprise a sponge, a colloidal suspension, or some other means of holding the fluid. In the present embodiment, the electrolytic fluid well 9 may be created by means of an adhesive collar that is either similar or identical to the adhesive collar 15 used to attach the electrode assembly to the packaging layer 1 and the subject or patient. If the electrolytic fluid 23 is infused into a sponge, said sponge may be any porous material placed inside the well for purposes of absorbing and holding electrolytic fluid 23. If the electrolytic fluid 23 is dispersed into a colloidal suspension, the continuous phase, or dispersion medium can be of any type that will readily absorb and hold the particular electrolytic fluid 23 being used while allowing the at least one surface feature or penetrator 21 of the electrode assembly to penetrate the medium 27 and become coated by the electrolytic fluid 23. The adhesive (not shown) used to attach the fluid well 9 to the lower surface 5 of the packaging layer 1 can be the same or similar as that used to attach the electrode assembly to the upper surface 3. Similar to the electrode assembly, the electrolytic fluid well 9 is attached to the lower surface 5 in such a manner that the well is aligned with the aperture or hole (not labeled) in the packaging base layer 1. As such, the at least one surface feature or penetrator 21 of the electrode assembly extends through the aperture and into the electrolytic well 9, more specifically into the electrolytic fluid medium 27, where it comes into contact with the electrolytic fluid 23 maintaining a coating of said fluid.

Alternatively, the electrolytic fluid well may comprise a multiple piece system (not shown) in which an open adhesive collar 15 is used and which requires the placement of a base layer (not shown) over the opening not in contact with the packaging base layer 1 to prevent loss or leakage of electrolytic fluid 23. Similarly, a multiple piece system as described could be used with the electrode assembly as well, where the base layer is attached to the opening of the electrode adhesive collar 15 and is further used to connect that collar to the electrode body 19.

The entire packaging portion depicted in the current figure is designed to be disposable. However, depending on the purposes for which the electrode or electrode array is being used, the packaging layer depicted here could be retained during monitoring in case the electrolytic fluid 23 needs to be reapplied to the surface of the surface feature or penetrator(s) 21. In such a situation, the electrode could be removed from the subject and pressed back onto the packaging system in a manner such that the surface feature or penetrator(s) 21 extend back into the medium 27 containing the fluid 23 thereby coating the surface of the surface feature or penetrator(s) 21 with fresh electrolytic fluid 23. The electrode could then be reapplied to the subject or patient for continued monitoring of the physiological signal.

Figure 5:
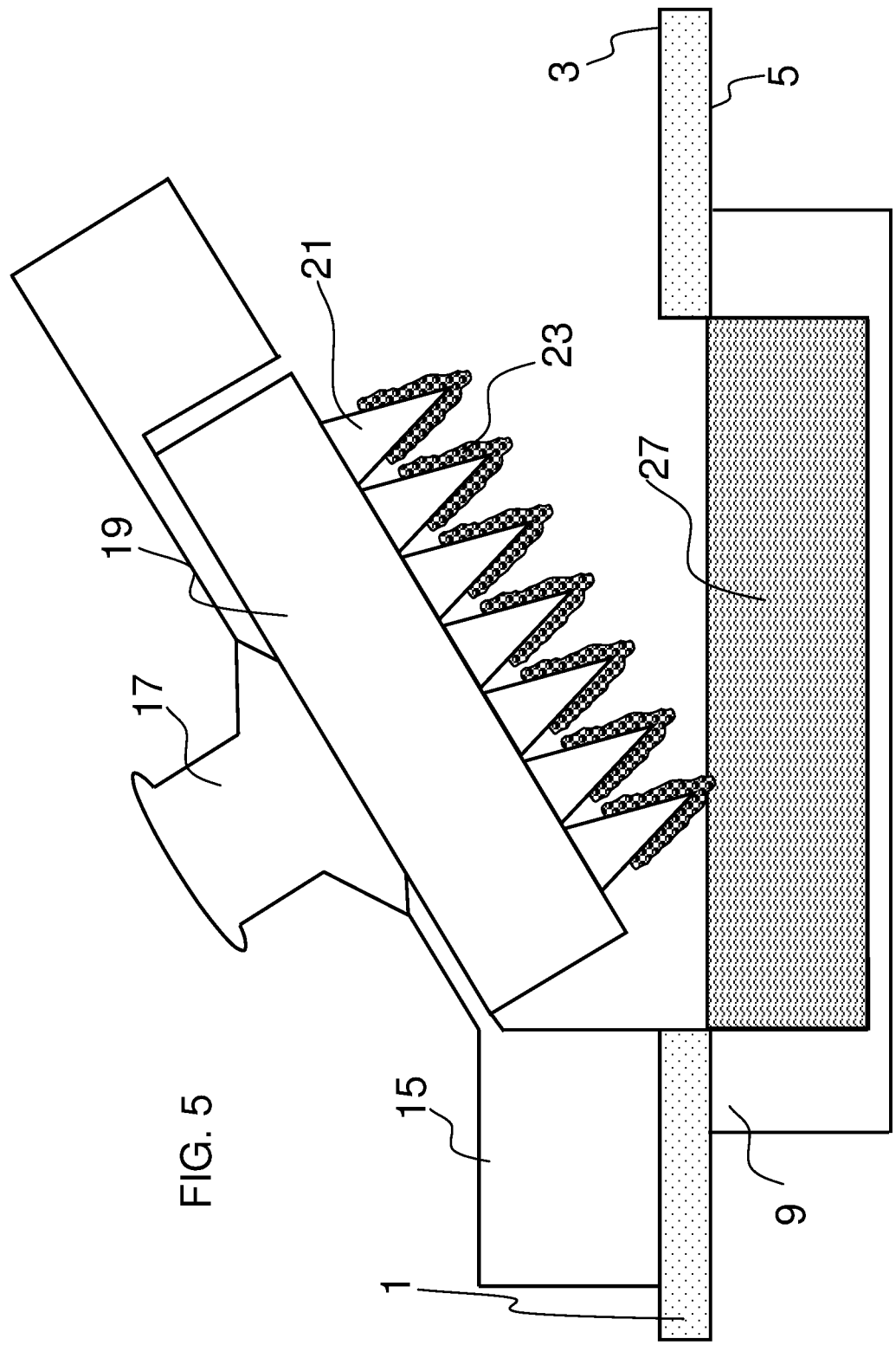
FIG. 5. Cross-sectional view of an electrode in the process of being lifted and separated from the packaging base layer, which is formed by a gel well attached to the bottom of a separator, with a coating of electrolytic fluid remaining on the surface feature or penetrator(s) of the electrode.

FIG. 5 is a cross-sectional view of the electrode assembly in the process of being removed from the packaging system comprising the base layer 1, electrolytic fluid well 9, and the medium 27 containing the electrolytic fluid 23.

One side of the electrode assembly has been detached from the packaging base layer 1 while the other side remains attached. The at least one surface feature or penetrator 21 lifts up and out of the medium 27 and remains coated with the electrolytic fluid 23 which is contained in the medium 27. As previously described, the medium 27 may be a sponge, a colloidal suspension, or some other medium capable of holding an electrolytic fluid 23 and also of allowing the at least one surface feature or penetrator 21 to enter said medium 27 and come in contact with the electrolytic fluid 23.

Figure 6:
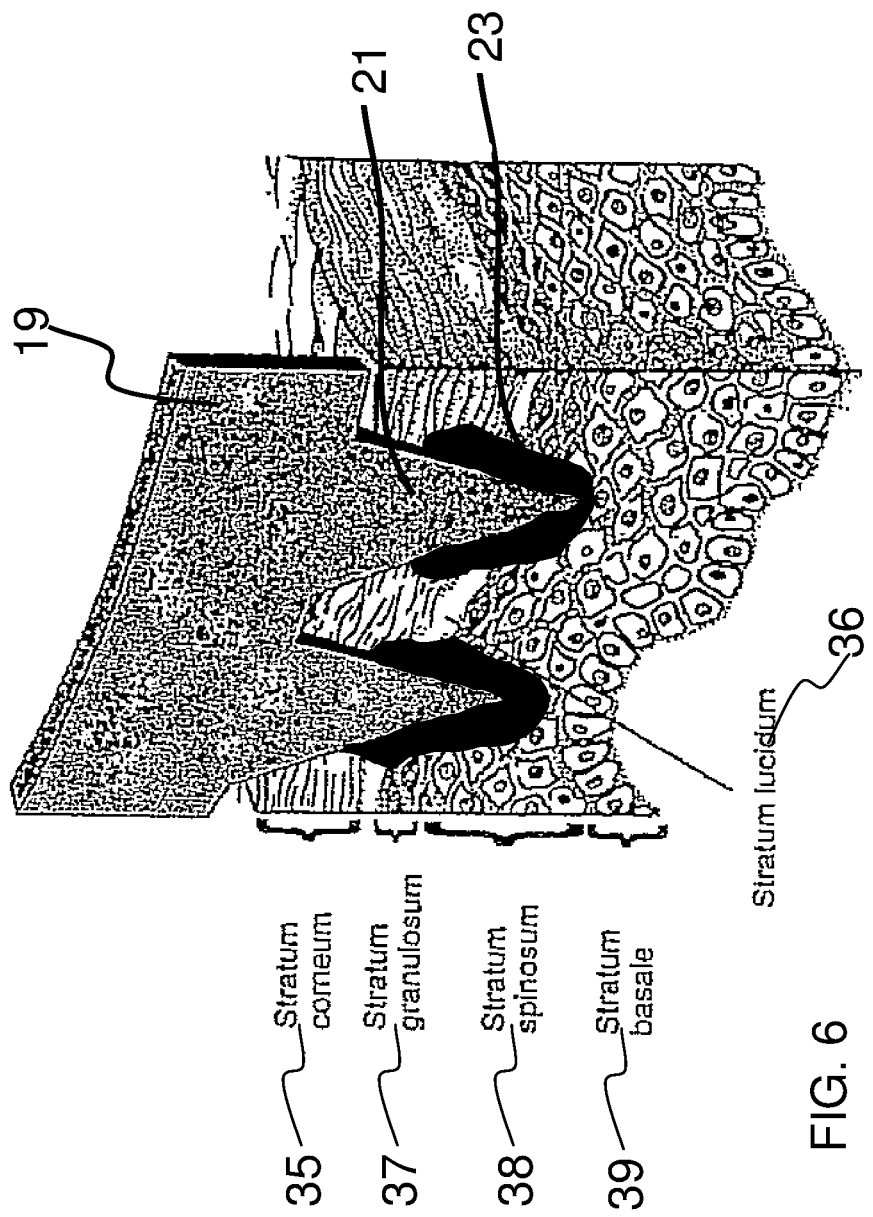
FIG. 6. Cross-sectional view of the layers of skin being and with surface feature or penetrators of an electrode piercing those layers.

FIG. 6 is a cross-sectional cut-away view of the typical epidermis layer of a subject's or patient's skin. The epidermis generally consists of the five outer layers of the skin, including the stratum corneum 35, the stratum lucidum 36, stratum granulosum 37, stratum spinosum 38, and stratum basale 39. This figure depicts the electrode, comprising the electrode body 19 and the surface feature or penetrator(s) 21, piercing through the outer layers of the skin, most importantly the stratum corneum 35. The stratum corneum 35 presents the greatest barrier to conductivity of physiological signals. The surface feature or penetrator(s) 21 pierce, break, or create entry through the stratum corneum 35 to the less electrically resistant layers and thereby collects and transmits a stronger, clearer physiological signal to the monitoring equipment (not shown). The surface feature or penetrator(s) 21 remain coated in electrolytic fluid 23 when removed from the packaging system thus further facilitating the conduction of the physiological signal to the monitoring equipment.

Figure 7:
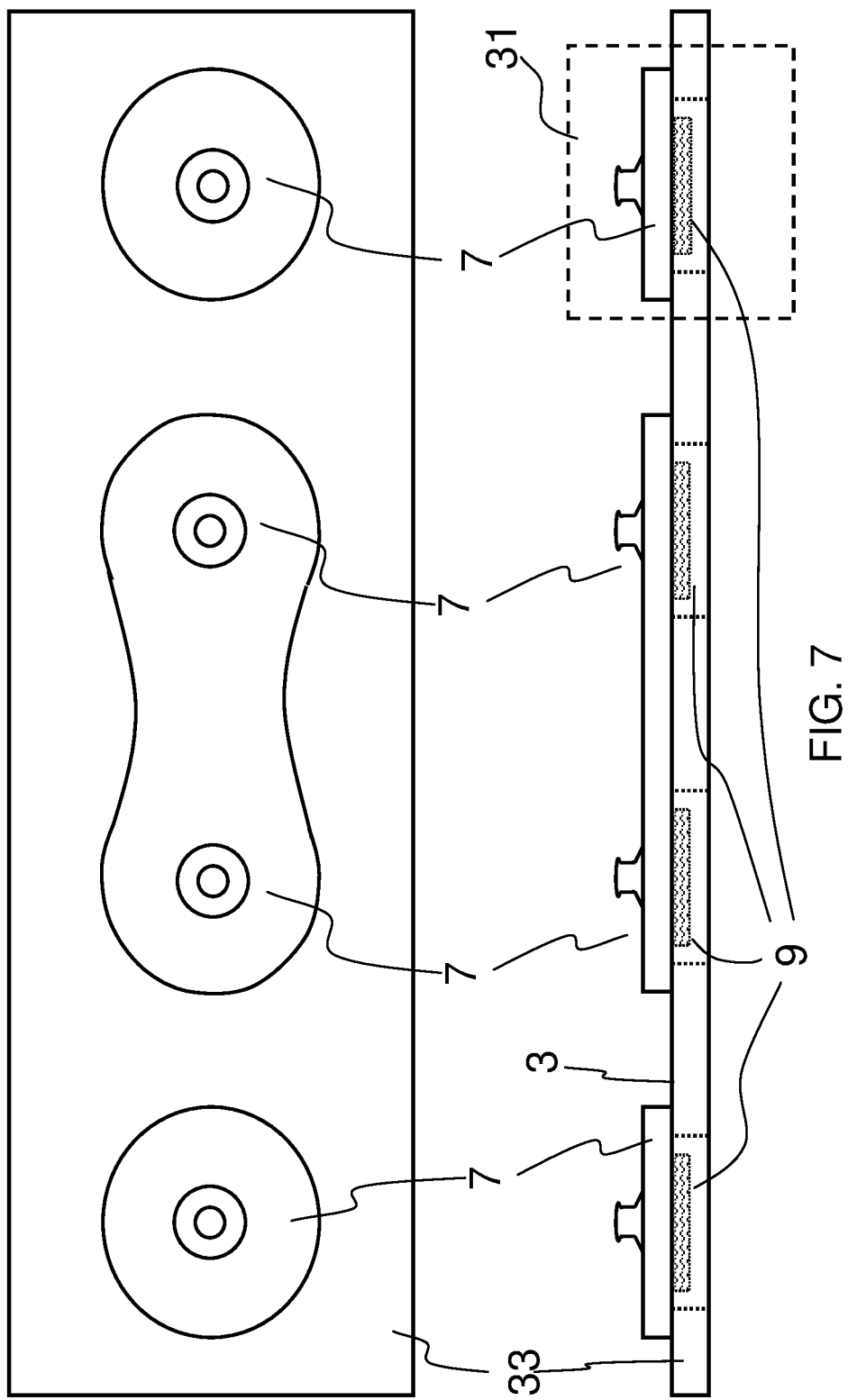
FIG. 7. Aerial and side views of one embodiment of electrodes packaged in an electrolytic gel well where the well is molded into the packaging base layer.

FIG. 7 is both an aerial and side view of one embodiment of the present invention wherein at least one physiological electrode 7 is packaged in such a manner that the at least one surface feature or penetrator 21 extends into a well 9 containing or holding electrolytic fluid 23. The electrolytic fluid 23 may be infused into a porous material 27 such as a sponge 27, it may be dispersed into a colloidal suspension 27 with some dispersion medium (not shown), it may be a viscous fluid with properties described herein contained by the well, or other method currently known or developed in the future. The packaging base layer 33 provides a substrate comprising an upper surface 3. Physiological recording electrodes or arrays comprising electrodes 7 (comprising at least a physiological recording electrode and an adhesive collar 15) are attached to the upper surface 3 via the attached adhesive collar 15. Although the figure depicts four such electrodes 7, the two center electrodes comprise a two electrode array, whereas the two outside electrodes 7 are individual electrodes. The upper surface 3 preferably comprises a smooth surface which allows for temporary adhesion of the electrode's 7 adhesive collar 15, but also allows the electrodes or electrode array to be removed without loss of the adhesive quality for secure attachment of the electrodes and electrode array to a subject or patient. The electrode(s) 7 are placed on the packaging layer 33 in such a manner that the electrode 7 is aligned with an aperture (not shown) through the packaging layer and at least one surface feature or penetrator 21 on the electrode extends into the packaging well 9. The well 9 preferably contains a sponge or other porous material 27 infused with electrolytic fluid 23, or a colloidal suspension 27 containing electrolytic fluid 23. The surface feature or penetrators 21 thereby remain bathed in the electrolytic fluid 23 throughout their time in the packaging regardless of how they are stored, and are thus coated with said fluid when removed from the packaging layer 33 and are ready for application onto a subject. Callout 31 is depicted in greater detail in FIGS. 8-10, and depicts various features of the present invention.

Figure 8:
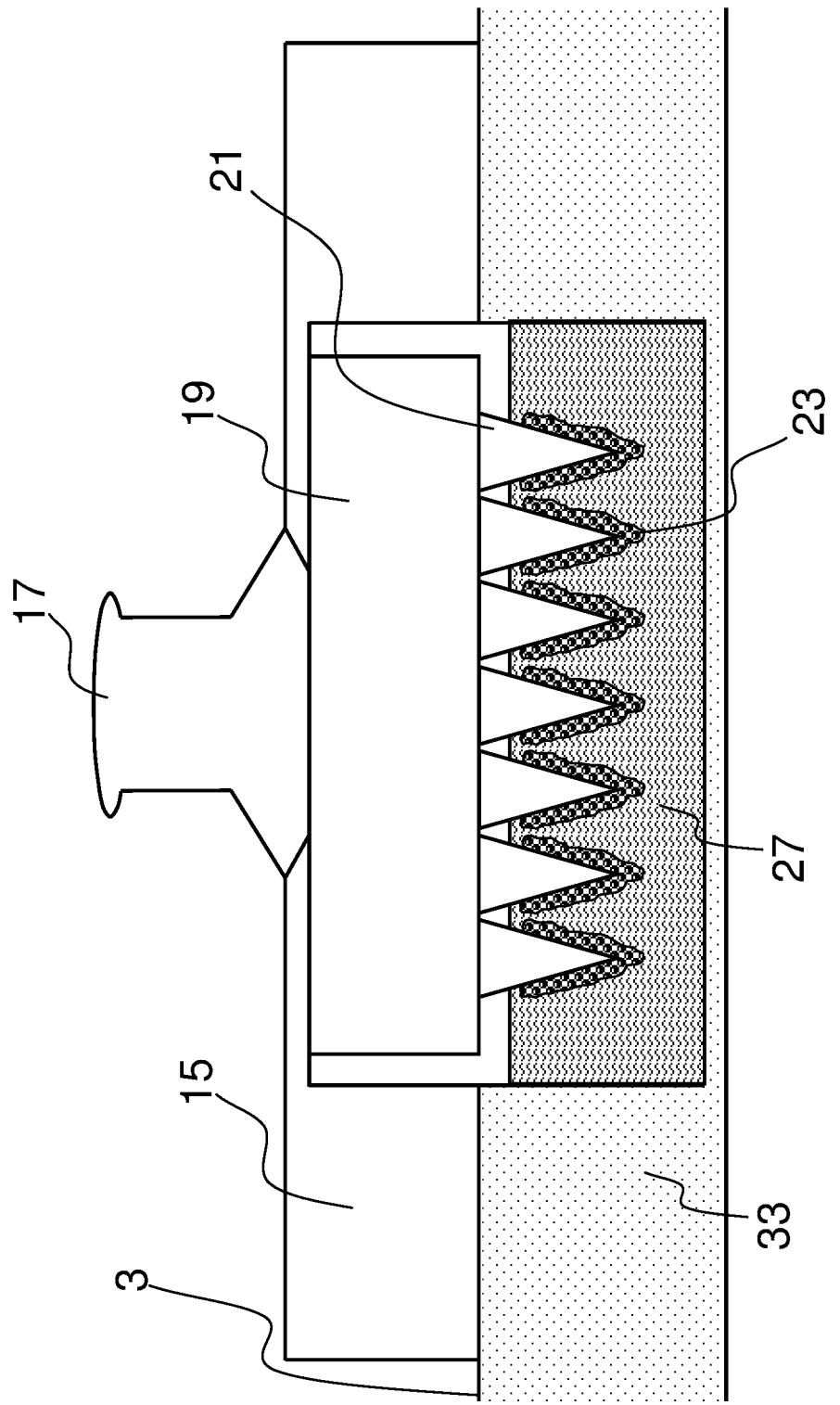
FIG. 8. Cross-sectional view of an electrode with surface feature or penetrators in a gel well that is molded into the packaging layer.

FIG. 8 is a cross-sectional view of one embodiment of the present invention wherein an electrode assembly is attached to a packaging system comprising a base layer further comprising an electrolytic fluid well.

In this particular embodiment, the packaging base layer 33 comprises a base of material such as plastic. This layer can be made of almost any type of plastic, including but not limited to polyvinyl chloride, polystyrene, polyamide, polyethylene, polypropylene, polyurethane, Teflon, and the like; though it is not limited only to plastics, and is designed to be used with other materials as well (i.e., metal, paper, rubber, and the like). The upper surface 3 of the packaging base layer 33, acts as an attachment surface for the electrode assembly. This upper surface 3 preferably is smooth and non-binding such that allows the electrode assembly to be removed from the surface without sticking and without loss of the adhesive substance (not shown) used to attach the electrode assembly to surfaces. In the present embodiment, the packaging base layer 33 itself comprises a solid piece which can be manufactured in any applicable manner (i.e., for plastic: injection molding, extrusion, and the like). The packaging base layer 33 further preferably comprises at least one depression, crater, hollow, or other such feature which creates a well (not labeled) such that the electrode assembly attached to the upper surface 3 can extend past the upper surface 3 of the base layer 33 and into said package.

The electrode assembly preferably comprises at least an adhesive collar 15, an electrode body 19, a connection node 17 which is attached to the electrode body 19, and at least one penetrator 21. The adhesive collar 15 preferably comprises a material such as a foam rubber or sponge-like material which provides flexibility as well as support, and an adhesive layer (not shown) which may consist of a very thin coating of said adhesive on the lower or outer portion of the collar. Also preferably, the electrode assembly contains at least one penetrator 21 as part of the electrode body 19 which is capable of piercing or creating an opening in a stratum corneum layer 35 or outer layer of a subject's skin. This electrode assembly is then placed in contact with the upper surface 3 of the packaging base layer 33 in such a manner that the electrode body 19 and the at least one penetrator 21 are in line with a well 9 in the base layer and the at least one penetrator 21 extends into the well 9 and is held in place by virtue of the adhesive (not shown) on the adhesive collar 15.

The electrolytic fluid well preferably comprises at least a pocket or well 9 bored, molded, or otherwise formed into the packaging base layer 33, and a medium 27 for holding electrolytic fluid which may comprise a sponge, a colloidal suspension, or some other device capable of holding the fluid in contact with the surface feature or penetrator 21. If the electrolytic fluid 23 is infused into a sponge 27, the sponge may be any porous material placed inside the well 9 for purposes of absorbing and holding electrolytic fluid. If the electrolytic fluid 23 is dispersed into a colloidal suspension or disc 27, the continuous phase, or dispersion medium can be of any type that will readily hold the particular electrolytic fluid being used while allowing the at least one surface feature or penetrator 21 of the electrode to be held in contact with the medium 27 and coated by the electrolytic fluid 23. When the electrode or electrode array 7 is attached to the upper surface 3 of the packaging base layer 33, the at least one surface feature or penetrator 21 of the electrode 7 extends through the aperture and into the electrolytic well 9, more specifically into the electrolytic fluid medium 27, where it comes into contact with the electrolytic fluid 23 maintaining a coating of said fluid on the surface feature or penetrator 21.

Figure 9:
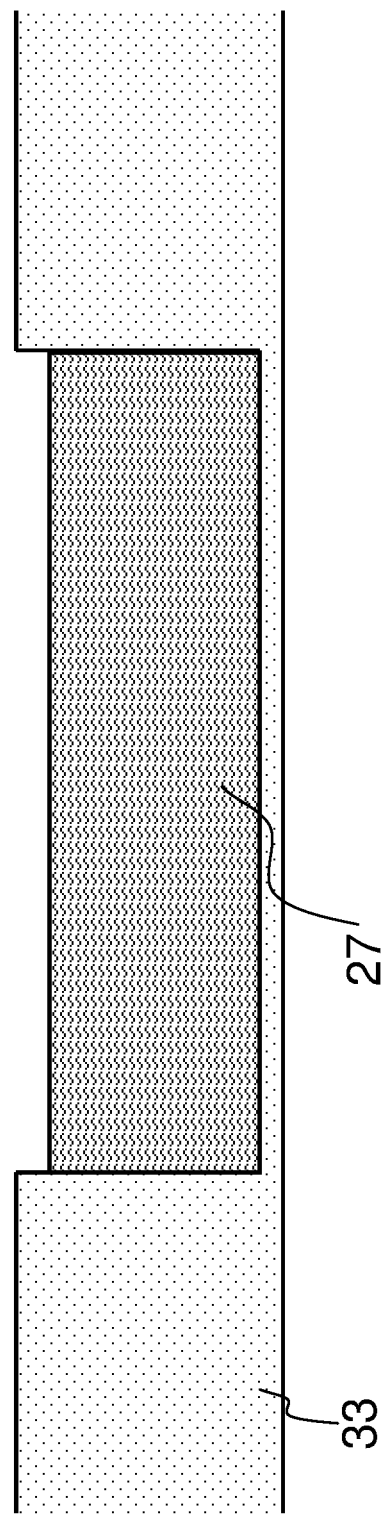
FIG. 9. Cross-sectional view of a gel well molded into the packaging base layer.

FIG. 9 The electrolytic fluid well preferably comprises at least a pocket or well 9 bored, molded, or otherwise formed into the packaging base layer 33, and a medium 27 for holding electrolytic fluid which may comprise a sponge, a colloidal suspension, or some other device capable of holding the fluid in contact with the surface feature or penetrator 21. If the electrolytic fluid 23 is infused into a sponge 27, the sponge may be any porous material placed inside the well 9 for purposes of absorbing and holding electrolytic fluid. If the electrolytic fluid 23 is dispersed into a colloidal suspension or disc 27, the continuous phase, or dispersion medium can be of any type that will readily hold the particular electrolytic fluid being used while allowing the at least one surface feature or penetrator 21 of the electrode to be held in contact with the medium 27 and coated by the electrolytic fluid 23.

The entire packaging portion depicted in the current figure is designed to be disposable. However, depending on the purposes for which the electrode or electrode array is being used, the packaging layer depicted here could be retained during monitoring in case the electrolytic fluid 23 needs to be reapplied to the surface of the penetrator(s) 21. In such a situation, the electrode could be removed from the subject and pressed back onto the packaging system in a manner such that the penetrator(s) 21 extend back into the medium 27 containing the fluid 23 thereby coating the surface of the penetrator(s) 21 with fresh electrolytic fluid 23. The electrode could then be reapplied to the subject or patient for continued monitoring of the physiological signal.

Figure 10:
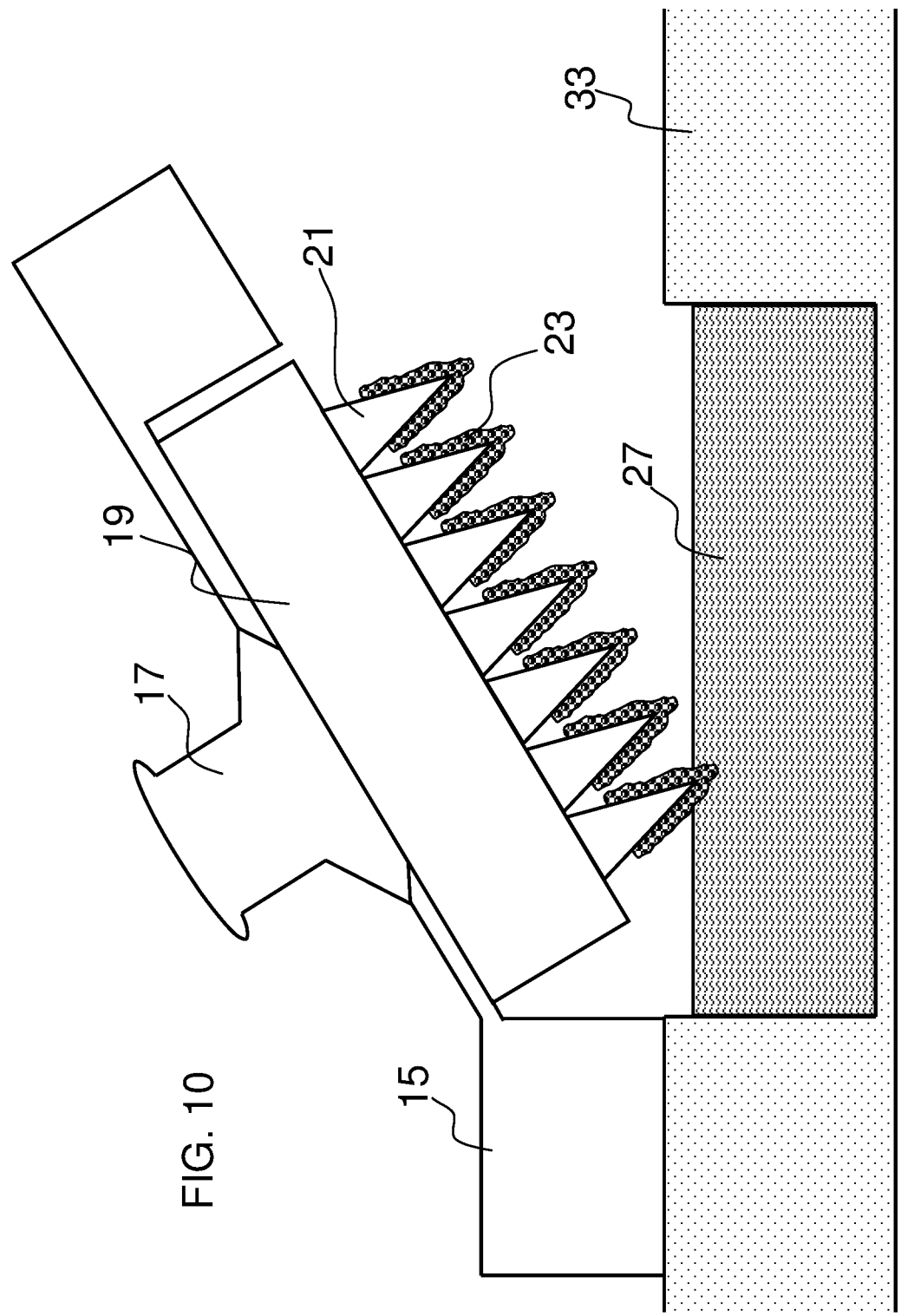
FIG. 10. Cross-sectional view of an electrode in the process of being lifted and separated from the packaging base layer, which is formed by a gel well molded into the packaging base layer, with a coating of electrolytic fluid remaining on the surface feature or penetrator(s) of the electrode.

FIG. 10 is a cross-sectional view of the electrode assembly in the process of being removed from the packaging system comprising the base layer 33, electrolytic fluid well 9, and the medium 27 containing the electrolytic fluid 23.

One side of the electrode assembly has been detached from the packaging base layer 33 while the other side remains attached. The at least one penetrator 21 lifts up and out of the medium 27 and remains coated with the electrolytic fluid 23 which is contained in the medium 27. As previously described, the medium 27 may be a sponge, a colloidal suspension, or some other medium capable of holding an electrolytic fluid 23 and also of allowing the at least one penetrator 21 to enter said medium 27 and come in contact with the electrolytic fluid 23.

Figure 11:
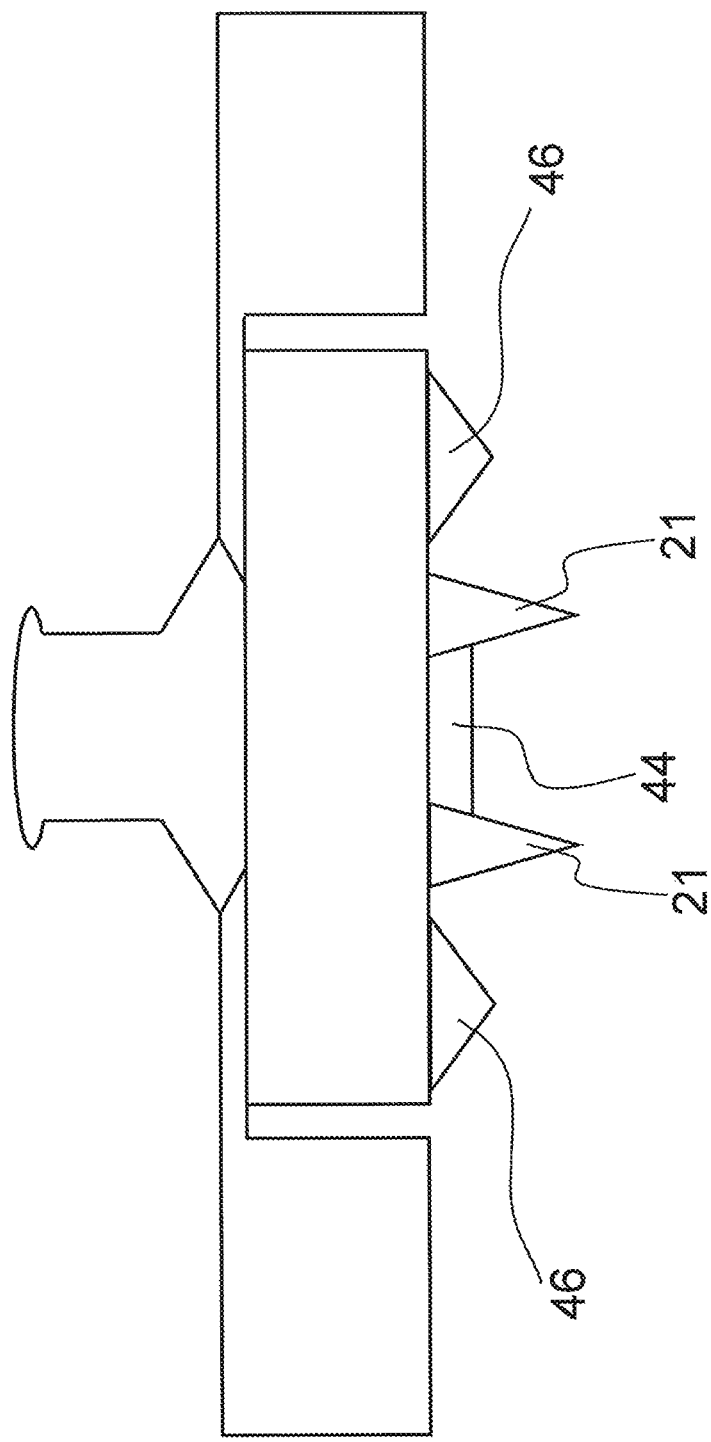
FIG. 11. Cross-sectional view of an electrode comprising various surface features including penetrators, anchors and epidermal stops.

FIG. 11 is a cross-sectional view of one embodiment of an electrode comprising various surface features including penetrators, anchors and an epidermal stop. The depicted electrode embodiment specifically is portrayed comprising penetrators 21, an epidermal stop 44, and anchors 46, all as described herein.

Figure 12:
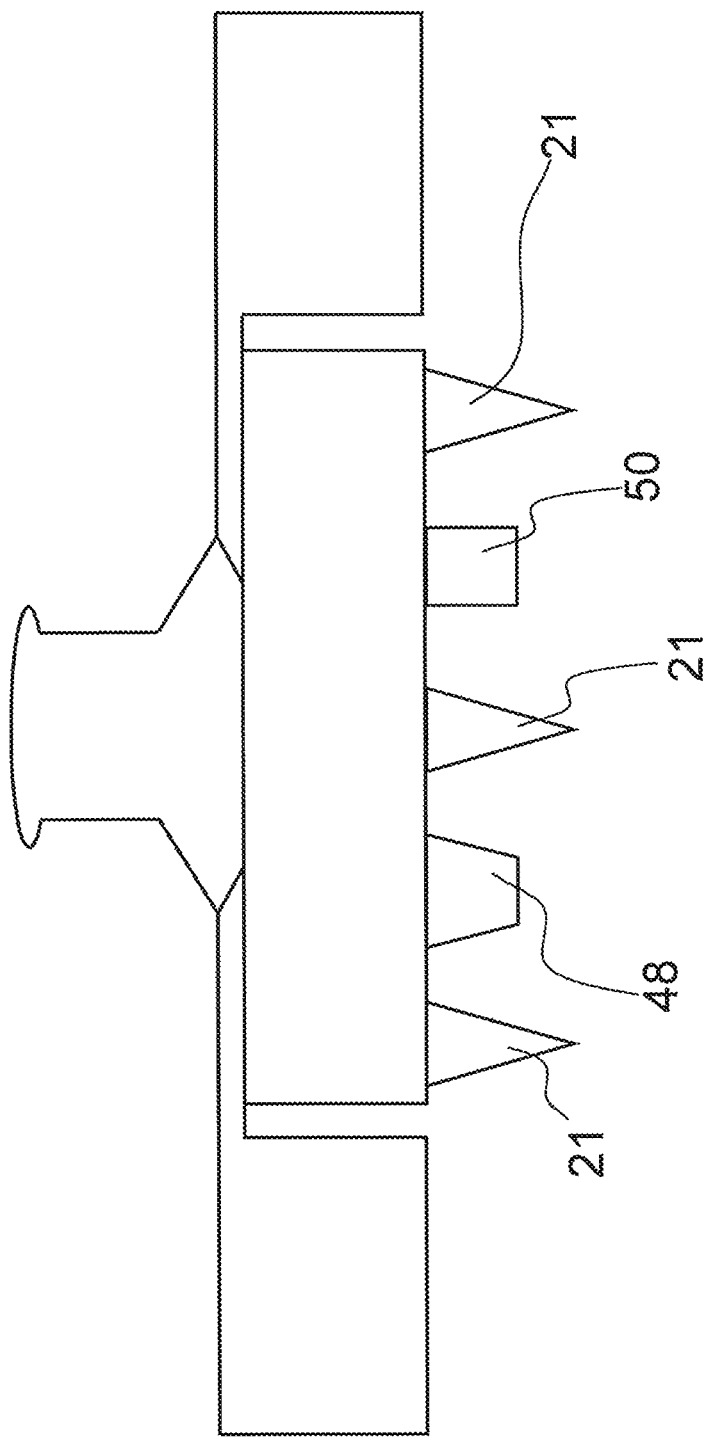
FIG. 12. Cross-sectional view of an electrode comprising various surface features including penetrators, ridges and columns.

FIG. 12 is a cross-sectional view of one embodiment of an electrode comprising various surface features including penetrators, a ridge and a column. The depicted electrode embodiment specifically is portrayed comprising penetrators 21, a ridge 48, and a column 50, all as described herein.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claims:

1. A physiological recording device comprising:
    a packaging base layer comprising a well containing an electrolytic fluid, gel or colloid; and
    at least one EEG physiological recording electrode, the at least one EEG physiological recording electrode comprising an upper and a lower surface, and at least one surface feature protruding from the lower surface of the EEG physiological electrode,
    wherein the electrolytic fluid, gel or colloid are at least in contact with the at least one surface feature of the EEG physiological recording electrode until the at least one surface feature of the physiological recording electrode is removed from the well for placement on a subject.

2. The physiological recording device of claim 1, wherein the at least one surface feature of the at least one EEG physiological electrode is selected from the group of surface features consisting of penetrators, ridges, columns, anchors and epidermal stops.

3. A physiological recording device comprising
    a packaging base layer comprising a well containing a colloidal suspension; and
    at least one EEG physiological recording electrode, the at least one EEG physiological recording electrode comprising an upper and a lower surface, and at least one surface feature protruding from the lower surface of the EEG physiological recording electrode
    wherein the colloidal suspension is at least in contact with the at least one surface feature of the EEG physiological recording electrode until the at least one surface feature of the EEG physiological recording electrode is removed from the well for placement on a subject.

4. The physiological recording device of claim 3, wherein the at least one surface feature of the at least one EEG physiological electrode is selected from the group of surface features consisting of penetrators, ridges, columns, anchors and epidermal stops.

5. A physiological recording device comprising:
    a packaging base layer comprising at least one well containing a colloidal suspension or a porous material with electrolytic fluid or gel infused in the porous material; and
    at least one EEG physiological recording electrode, the at least one EEG physiological recording electrode comprising an upper and a lower surface, and at least one surface features protruding from the lower surface of the EEG physiological recording electrode,
    wherein the sponge holds the electrolytic fluid in contact with the at least one surface features of the EEG physiological recording electrode until the at least one surface feature of the physiological recording electrode is removed from the well for placement on a subject.

6. The physiological recording device of claim 5, wherein the at least one surface feature is from the group of surface features consisting of penetrators, ridges, columns, anchors and epidermal stops.

* * * * *